Figure 1:
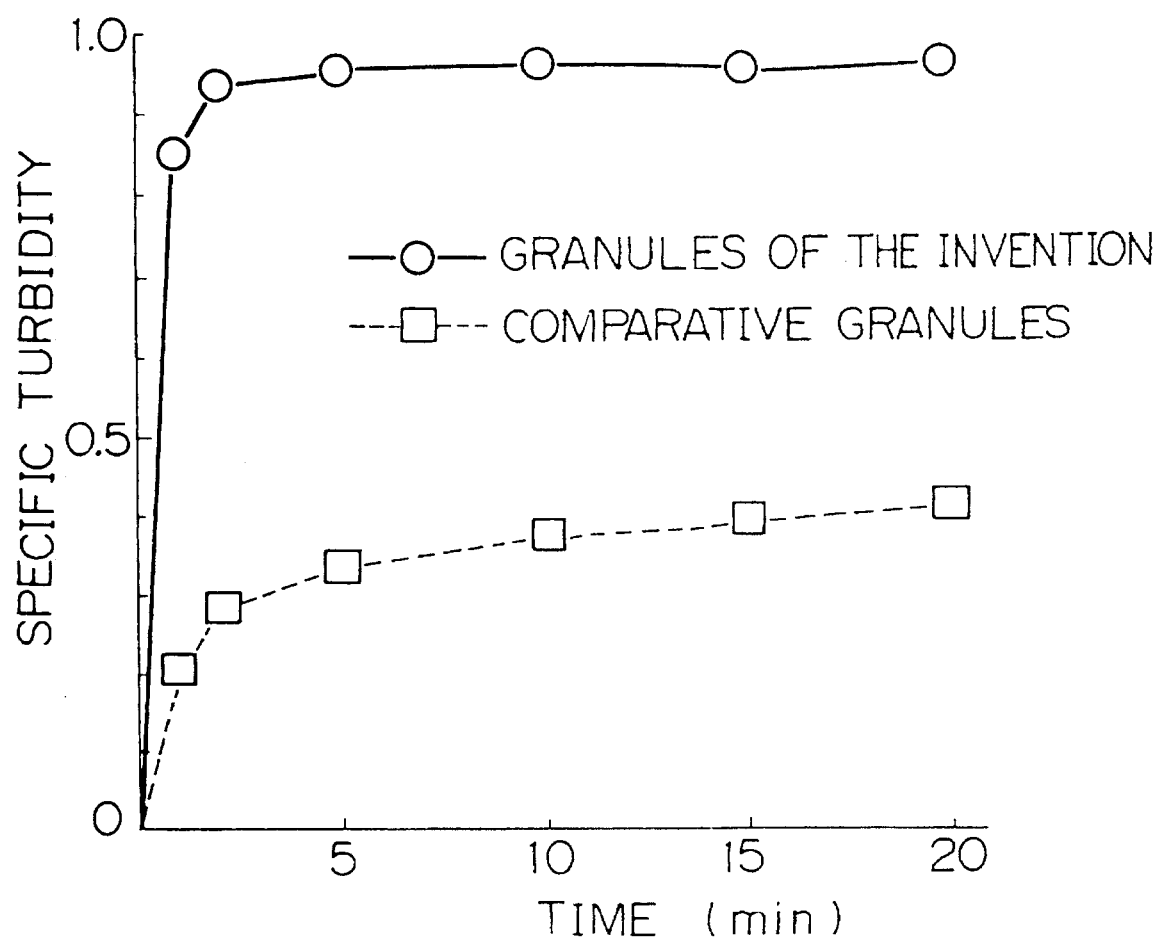

United States Patent [19]

Iida et al.

[11] Patent Number: 5,547,943
[45] Date of Patent: Aug. 20, 1996

[54] SUCRALFATE PREPARATION

[75] Inventors: Yoshimitsu Iida, Saitama-ken; Minoru Machida, Tokyo, both of Japan

[73] Assignee: Chugai Seiyaku Kabushiki Kaisha, Tokyo, Japan

[21] Appl. No.: 306,202

[22] Filed: Feb. 2, 1989

Related U.S. Application Data

[63] Continuation-in-part of Ser. No. 42,884, Apr. 27, 1987, abandoned.

[30] Foreign Application Priority Data

Apr. 30, 1986 [JP] Japan .................................. 61-99901

[51] Int. Cl.$^6$ .................................................. A61K 31/70
[52] U.S. Cl. ........................... 514/53; 514/925; 514/927; 424/78
[58] Field of Search ........................... 514/53, 925, 927; 424/78; 536/118

[56] References Cited

U.S. PATENT DOCUMENTS

| | | | |
|---|---|---|---|
| 3,432,489 | 3/1969 | Nitta et al. ................................ | 536/118 |
| 4,454,152 | 6/1984 | Barry et al. ................................ | 424/78 |
| 4,457,932 | 7/1984 | Juby et al. ................................ | 424/251 |
| 4,547,496 | 10/1985 | Kumazawa et al. ..................... | 514/218 |
| 4,668,665 | 5/1987 | Ishihara et al. .......................... | 514/53 |

OTHER PUBLICATIONS

The Merck Index, 9th ed (1976) published by Merck & Co., Inc. pp. 983–984, No. 7349.

*Primary Examiner*—Elli Peselev
*Attorney, Agent, or Firm*—Browdy and Neimark

[57] ABSTRACT

A preparation containing an aluminum salt of a sucrose sulfate ester (sucralfate) and polyethylene glycol, and a process for preparation of the same are disclosed. Sucralfate is extensively used as a curative for digestive ulcers and has the capability of protecting the substrate protein. Sucralfate is mixed with polyethylene glycol to provide it with improved disintegrability and dispersibility and this renders sucralfate more useful as a medicine.

9 Claims, 2 Drawing Sheets

5,547,943

SUCRALFATE PREPARATION

This application is a continuation-in-part of parent, application Ser. No. 042,884, filed Apr. 27, 1987, now abandoned without prejudice in favor of the present application.

The present invention relates to an aluminum salt of a sucrose sulfate ester (conventionally known as sucralfate) preparation and a process for producing such sucralfate preparation. According to the process of the present invention, sucralfate is mixed with polyethylene glycol to be provided with enhanced disintegrability and dispersibility and this renders sucralfate more useful as a medicine.

Sucralfate is extensively used as a curative for digestive ulcers as it has the capability to protect the substrate protein (ability to protect the gastric mucosa) and to suppress the activity of pepsin in gastric juice as well as having antiacid effects. It is generally understood that sucralfate binds strongly with the protein component of fur on the bottom of an ulcer to form a layer that chemically protects the affected area from the strong digestive power of gastric juice and thereby promotes the healing process (Nakazawa, S. et al., Dig. Dis. Sci., 2.6, 297 (1981); and A. Ishimori et al., Igaku to Yakugaku, 9, 25 (1983)).

On the other hand, sucralfate is insoluble in water and its preparations must be readily disintegrated and dispersed in order for them to become effectively bound to the area affected by an ulcer.

The present inventors conducted various studies in order to develop a sucralfate preparation that has improved disintegrability and dispersibility. As a result, the present inventors have found that this object can be attained by mixing sucralfate with polyethylene glycol. The present invention has been accomplished on the basis of this finding.

Figure 2:
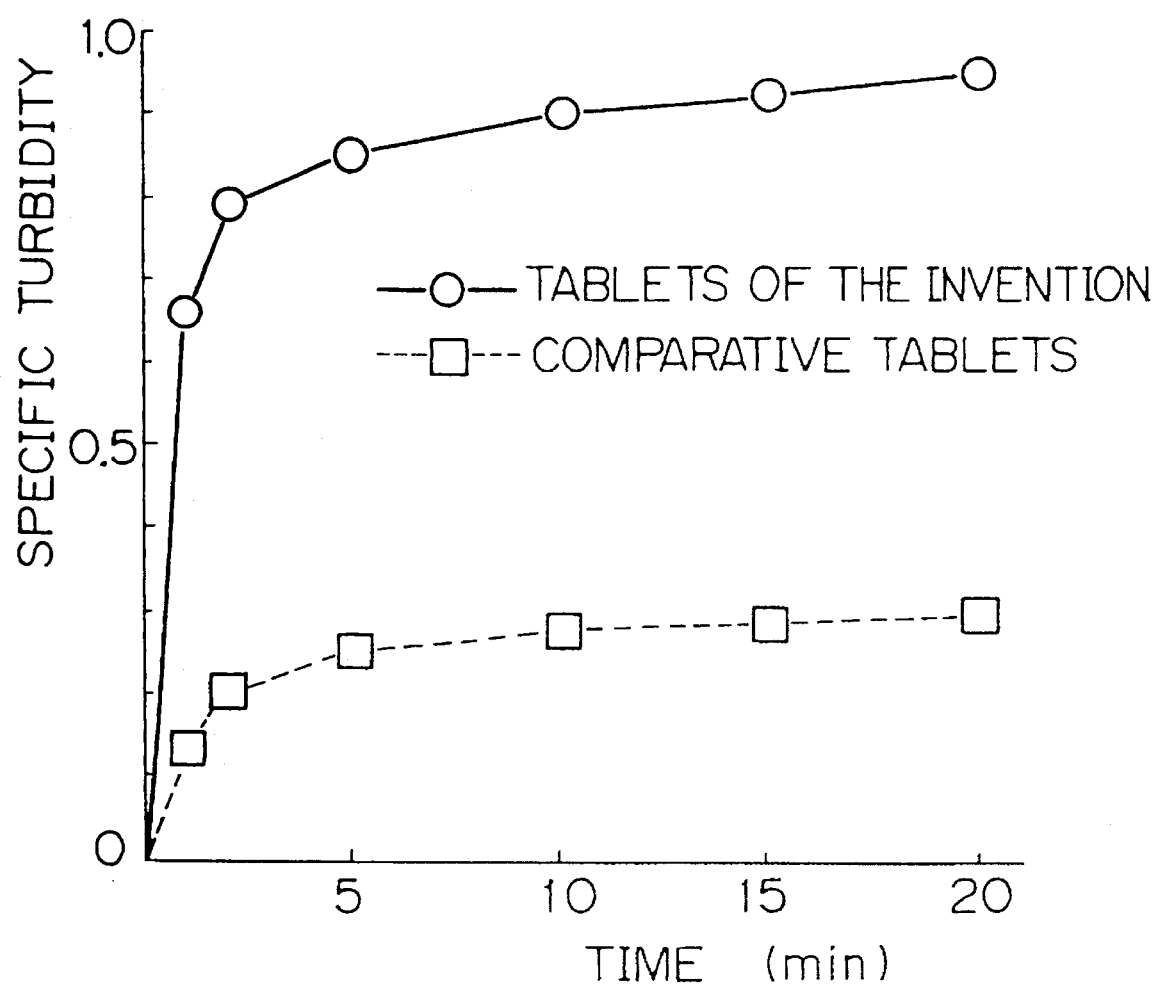

FIGS. 1 and 2 show the profiles of disintegration and dispersion of sucralfate preparations that were made in accordance with the present invention and comparative preparations.

According to the present invention, a sucralfate is mixed with 0.1% (w/w) or more, preferably 1–7%, and most preferably 3–7%, of polyethylene glycol. Although the upper limit of polyethylene glycol is not critical, it may be usually used in an amount of less than 50% (w/w). The molecular weight of the polyethylene glycol to be mixed with the sucralfate is not limited to any particular value, although the average molecular weight of the PEG is preferably 1,000–8,000, most preferably 1,500–6,000. When administered perorally, the sucralfate preparation of the present invention will allow the sucralfate to become effectively bound to the ulcer-affected area. The sucralfate preparation of the present invention may be formulated in various dosage forms such as powders, fine granules, granules, tablets and capsules. For this purpose, various additives may be used such as binders, disintegrators, lubricants, excipients and coloring agents.

The following examples are provided for the purpose of further illustrating the present invention but are in no sense to be taken as limiting.

EXAMPLE 1

An aluminum salt of sucrose sulfate ester (sucralfate: 3,920 g) was intimately blended with 2,000 g of an aqueous solution of 4% polyethylene glycol (mol. wt. 1,500) in a mixer. The mixture was granulated in a cylindrical granulator provided with a net having a mesh size of 0.7 mm$^\phi$. The granulation was dried at 60° C. for 3 hours in a tray dryer. The dried granulation was screened through a 16-mesh sieve to make granules. Comparative granules were prepared by the same method as described above except that the aqueous solution of 4% polyethylene glycol was replaced by water.

The disintegrability and dispersibility of the two samples of granules are shown in FIG. 1 in terms of the change in turbidity that occurred with the value of a control suspension being taken as 1. The control suspension was prepared by well dispersing 1 g of a sucralfate in 1,000 ml of water with ultrasonic waves and the turbidity of this control suspension was measured at 540 nm with the thickness of the layer in the detector cell being 1 cm. Measurement of turbidity is described more specifically below: suspensions each containing 200 mg of sucralfate were charged into five auxiliary tubes in a disintegration tester (test fluid: 1,000 ml of water at 37°±2° C.) and the turbidities of fluid portions sampled at about 5 cm below the surface of the test fluids were measured. Based on the data obtained, the specific turbidities of the individual samples were then calculated.

The two samples of granules were subjected to an acceleration test at 40° C.×75% r.h. for 6 months and the state of their dispersion was evaluated in terms of specific turbidity that was calculated in the manner described above. The results are shown in Table 1.

TABLE I

Change in Specific Turbidity as a Result of Acceleration at 40° C. × 75% r.h. for 6 months

| Sample | | Time | | |
| --- | --- | --- | --- | --- |
| | | 2 min. | 5 min. | 20 min. |
| Granules of the invention | before acceleration | 0.93 | 0.95 | 0.96 |
| | after acceleration | 0.85 | 0.92 | 0.95 |
| Comparative granules | before acceleration | 0.28 | 0.33 | 0.41 |
| | after acceleration | 0.16 | 0.18 | 0.19 |

EXAMPLE 2

Sucralfate (4,000 g) was intimately blended with 2,000 g of an aqueous solution of 10% polyethylene glycol (tool. wt. 6,000) in a mixer. The mixture was sifted through a 16-mesh screen to make a granulation, which was dried at 60° C. for 3 hours in a tray dryer and classified by passage through a 10-mesh screen.

The resulting granules (4,000 g) were mixed with 1,376 g of crystalline cellulose and 24 g of magnesium stearate and blended for 5 minutes in a V-type mixer.

The resulting powder was set in a rotary tableting machine equipped with dies and punches (12 mm$^\phi$) and compressed under a total pressure of about 2.5 tons to make tablets each weighing 700 mg.

Comparative tablets were made in the same manner as described above except that the aqueous solution of 10% polyethylene glycol was replaced by an aqueous solution of 10% hydroxypropyl cellulose (Nisso HPC-L of Nippon Soda Co., Ltd.)

The disintegrability and dispersibility of the two samples of tablets are shown in FIG. 2 in terms of the change in turbidity that occurred with the value of a control suspension being taken as 1. The control suspension was prepared by well dispersing 1,000 mg of sucralfate, 344 mg of crystalline cellulose and 6 mg of magnesium stearate in 1,000 ml of water with ultrasonic waves and the turbidity of this control suspension was measured at 540 nm in a detector cell having a layer thickness of 1 cm. Measurement of turbidity is described more specifically below: two tablets of each sample were set in a disintegration tester (test fluid: 1,000 ml of water at 37°±2° C.) and the turbidities of fluid portions sampled at about 5 cm below the surface of the test fluids were measured. Based on the data obtained, the specific turbidities of the individual samples were calculated.

The two samples of tablets were subjected to an acceleration test at 40° C.×75% r.h. for 6 months and the state of their dispersion was evaluated in terms of specific turbidity that was calculated in the manner described above. The results are shown in Table 2.

TABLE 2

Change in Specific Turbidity as a Result of Acceleration at 40° C. × 75% r.h. for 6 months

| Sample | | Time | | |
| --- | --- | --- | --- | --- |
| | | 2 min. | 5 min. | 20 min. |
| Tablets of the invention | before acceleration | 0.79 | 0.85 | 0.95 |
| | after acceleration | 0.63 | 0.80 | 0.92 |
| Comparative tablets | before acceleration | 0.20 | 0.25 | 0.30 |
| | after acceleration | 0.09 | 0.13 | 0.16 |

What is claimed is:

1. A pharmaceutical composition in solid form which consisting eventually of an effective ulcer-treating amount of an aluminum salt of a sucrose sulfate ester and 1–7% (w/w) of polyethylene glycol on the basis of said sucrose sulfate ester.

2. A pharmaceutical composition in solid form according to claim 1 wherein said composition is prepared by dissolving polyethylene glycol in an amount of 1–7% (w/w) based on the aluminum salt of a sucrose sulfate ester in water, an alcohol or a mixture thereof, adding to the resulting solution the aluminum salt of a sucrose sulfate ester and then drying the mixture.

3. A pharmaceutical composition in the form of granule according to claim 1.

4. A pharmaceutical composition in the form of tablet according to claim 1.

5. A pharmaceutical composition in the solid form according to claim 1 wherein the average molecular weight of said polyethylene glycol ranges from 1,500 to 6,000.

6. A pharmaceutical composition in solid form according to claim 1, wherein the average molecular weight of said polyethylene glycol ranges from 1,000 to 8,000.

7. A pharmaceutical composition in the form of granule according to claim 2.

8. A pharmaceutical composition in the form of tablet according to claim 2.

9. A pharmaceutical composition according to claim 2 wherein an excipient is also added to said resulting solution along with said aluminum salt of a sucrose sulfate ester.

* * * * *